United States Patent [19]
Adler-Golden et al.

[11] Patent Number: 5,822,058
[45] Date of Patent: Oct. 13, 1998

[54] SYSTEMS AND METHODS FOR OPTICALLY MEASURING PROPERTIES OF HYDROCARBON FUEL GASES

[75] Inventors: Steven Adler-Golden, Newtonville; Lawrence S. Bernstein, Lexington; Fritz Bien, Concord; Michael E. Gersh, Bedford; Neil Goldstein, Belmont, all of Mass.

[73] Assignee: Spectral Sciences, Inc., Burlington, Mass.

[21] Appl. No.: 784,608

[22] Filed: Jan. 21, 1997

[51] Int. Cl.$^6$ .................................................... G01J 3/40
[52] U.S. Cl. .......................... 356/303; 356/300; 356/301; 356/302; 356/311; 356/320
[58] Field of Search .................................... 356/303, 300, 356/301, 302, 311, 320

[56] References Cited

U.S. PATENT DOCUMENTS

| | | |
|---|---|---|
| 4,198,859 | 4/1980 | Holtermann . |
| 4,288,062 | 9/1981 | Gupta et al. . |
| 4,303,194 | 12/1981 | Kengle et al. . |
| 4,306,451 | 12/1981 | Szonntagh . |
| 4,315,430 | 2/1982 | Szonntagh . |
| 4,359,284 | 11/1982 | Kude et al. . |
| 4,386,858 | 6/1983 | Kude et al. . |
| 4,492,862 | 1/1985 | Grynbert et al. . |
| 4,613,482 | 9/1986 | Cheney . |
| 4,800,279 | 1/1989 | Hieftje et al. ........................... 250/339 |
| 4,951,503 | 8/1990 | Fini . |
| 4,958,076 | 9/1990 | Bonne et al. . |
| 4,994,671 | 2/1991 | Safinya et al. . |
| 5,078,593 | 1/1992 | Schreiber, Jr. et al. . |
| 5,223,714 | 6/1993 | Maggard . |
| 5,224,776 | 7/1993 | Clingman, Jr. et al. . |
| 5,235,844 | 8/1993 | Bonne et al. . |
| 5,310,335 | 5/1994 | van Berkum . |
| 5,311,447 | 5/1994 | Bonne . |
| 5,349,189 | 9/1994 | Maggard . |
| 5,370,790 | 12/1994 | Maggard et al. . |
| 5,412,581 | 5/1995 | Tackett . |
| 5,452,232 | 9/1995 | Espinosa et al. . |
| 5,475,612 | 12/1995 | Espinosa et al. . |
| 5,490,085 | 2/1996 | Lambert et al. . |
| 5,491,344 | 2/1996 | Kenny et al. ........................ 250/461.1 |
| 5,494,826 | 2/1996 | Stetter et al. . |
| 5,572,030 | 11/1996 | Ranson et al. ..................... 250/339.12 |

FOREIGN PATENT DOCUMENTS

WO94/08226   4/1994   WIPO .

OTHER PUBLICATIONS

Williamson, J., et al., "Near–Infrared Raman Spectroscopy with a 783–nm Diode Laser and CCD Array Detector", Applied Spectroscopy (vol. 43, No. 3, 1989).

Schwab, Scott D., et al., "Versatile, Efficient Raman Sampling with Fiber Optics", Analytical Chemistry, 56 (1984) Oct.

Brown, Christopher B., et al., "Optical BTU Sensor Development", Final Report, Jul. 1993.

Kelly, Jeffrey J., "Prediction of Gasoline Octane Numbers from Near–Infrared Spectral Features in the Range 660–1215nm", American Chemical Society, 1989.

Swarin, J. Stephen and Drumm, Charlene A., "Predicting Gasoline Properties Using Near–IR Spectroscopy", Spectroscopy 7(7) 1992.

*Primary Examiner*—David C. Nelms
*Assistant Examiner*—Reginald A. Ratiff
*Attorney, Agent, or Firm*—Hamilton, Brook, Smith & Reynolds, P.C.

[57] ABSTRACT

A system and method for optical interrogation and measurement of a hydrocarbon fuel gas includes a light source generating light at near-visible wavelengths. A cell containing the gas is optically coupled to the light source which is in turn partially transmitted by the sample. A spectrometer disperses the transmitted light and captures an image thereof. The image is captured by a low-cost silicon-based two-dimensional CCD array. The captured spectral image is processed by electronics for determining energy or BTU content and composition of the gas. The innovative optical approach provides a relatively inexpensive, durable, maintenance-free sensor and method which is reliable in the field and relatively simple to calibrate. In view of the above, accurate monitoring is possible at a plurality of locations along the distribution chain leading to more efficient distribution.

60 Claims, 10 Drawing Sheets

SYSTEMS AND METHODS FOR OPTICALLY MEASURING PROPERTIES OF HYDROCARBON FUEL GASES

GOVERNMENT RIGHTS

The U.S. Government may have certain rights in the invention under Department of Energy grant No. DE-F602-96ER822280.

BACKGROUND

A key requirement for efficient and cost-effective use of natural gas is the ability for real-time, on-line monitoring of its chemical composition and BTU (i.e., energy, caloric or thermal) content. Monitoring is required along the entire distribution network, from gas storage and distribution facilities to industrial consumers.

Calorimeters and gas chromatographs (GCs) are currently used for this purpose; however, they require sheltering from the elements and removal of samples from the pipeline, they have a slow response (1 minute or greater), and they are expensive in terms of initial cost (around $20,000 each for a GC), installation, and required maintenance. In addition, calorimeters do not measure the gas composition, which is needed to calculate such properties as the dew point, compressibility, and Wobbe index.

In recent years, optical absorption methods for measuring natural gas at infrared (IR) wavelengths have been proposed and investigated. Such systems are not suitable for commercial use as the detector technology at IR wavelengths can be prohibitively expensive.

There is a continuing need for improvement in systems and methods for monitoring gaseous hydrocarbons, particularly natural gases, that are inexpensive, fast and accurate.

SUMMARY OF THE INVENTION

To overcome the limitations of the prior art, the present invention is directed to a rugged, inexpensive and maintenance-free optical sensor having a BTU measurement accuracy that matches currently-available systems. The present invention relates to a BTU and composition sensor for fluid hydrocarbons using an innovative optical approach. The approach involves a spectral measurement of absorption bands of the hydrocarbon components (principally methane and ethane, with smaller amounts of propane, butanes, and pentanes) at near-visible wavelengths with available, low-cost silicon detector technology. The spectral measurement yields both the total BTU content and compositional information, including the concentration of methane and combinations of the higher hydrocarbons. A preferred embodiment of the invention is a sensor for natural gas pipelines that can be for either indoor or outdoor installation, has a fast time response (10 seconds or less), and complies with the Class 1, Division 1 safety requirements.

There are several important advantages afforded by working at near-visible wavelengths, as opposed to the infrared regions which have been previously investigated for optical sensing. The first advantage is low fabrication cost. Dramatic cost and performance improvements in silicon array detectors such as charge coupled devices (CCDs), CID and CMOS detectors and the associated processing electronics, which are mass-produced for video cameras, permit rugged, compact, and inexpensive spectrograph systems to be constructed that have excellent response and resolution at near-visible wavelengths (700–1000 nm). With this type of optical system, methane spectral structure can be resolved, providing an automatic wavelength reference. Furthermore, the absorption strengths in this spectral region are closely correlated with BTU content, making a complete compositional analysis unnecessary.

Lower-resolution IR techniques, for example, those employing multiple discrete detectors, light sources, or filters, can aid in lowering the manufacturing cost, but these techniques pose difficult and expensive calibration problems due to nonlinear dependencies of absorbance on number density as well as sensor-to-sensor differences in the response of each wavelength channel.

A second advantage of the present invention is simplicity of calibration. The 2 nm FWHM resolution of a CCD spectrograph is sufficient to resolve the methane spectral structure, providing an automatic wavelength reference which eliminates calibration problems that have occurred in previous field instruments. Moreover, the observed linearity of absorbance with number density (Beer's law behavior), which does not hold well at longer wavelengths and lower resolution, greatly simplifies both the development of the instrument and the calibration of individual sensors. For example, instead of requiring an empirical chemometric calibration, which involves preparing perhaps 50 different component mixtures and measuring each manufactured sensor at multiple pressures and temperatures, only one or two measurements for each-pure hydrocarbon at a given temperature are required to be performed only for one sensor to define a complete and robust calibration valid for all of the sensors. Small differences among individual sensors in a production run, which are related to the path length, wavelength registration, pressure reading, etc., can all be taken into account by calibrating each sensor on only one or two standard BTU gases.

A third advantage is the operational simplicity afforded by using a two-dimensional detector array, which enables the simultaneous acquisition of both sample and reference spectra. In contrast, prior art systems employing either linear arrays or multiple discrete detectors can take only one spectrum at a time, and therefore require continuous cycling between sample and reference gases in order to generate an accurate absorbance measurement. A two-dimensional IR array avoids this sampling complication. Furthermore obtaining simultaneous sample and reference spectra obviates the requirement to maintain a constant detector array temperature during the cycle between separate sample and reference spectra.

In view of the above, a preferred embodiment of the present invention is directed to an apparatus and method for measuring properties of natural gases. The apparatus of the invention comprises a light source for generating light at near-visible wavelengths. A measurement cell in fluid communication with a pipeline and containing a hydrocarbon fuel natural gas sample is optically coupled to the light source. Light from the light source interrogates the gas in the cell. A spectrograph receives the transmitted light and can include a grating for dispersing the light. A sensor responsive to the dispersed light collects an electronic spectral representation thereof. Electronics processes the collected representation to determine properties of the gas.

In a preferred embodiment, the determined properties include BTU (energy) content and composition of the natural gas sample. The sensor preferably comprises a silicon sensor array, for example a two-dimensional CCD array. The light generated by the source is preferably divided into a sample beam for interrogation of the sample and a reference beam for direct transmission into the spectrograph. Both beams are processed by the spectrograph and used for subsequent calculations. The wavelength of the light source is preferably in the range between 700 and 1000 nm. The spectral resolution is preferably sufficient to resolve structure in the methane absorption band near 900 nm.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

DETAILED DESCRIPTION OF PREFERRED EMBODIMENTS

Figure 1:
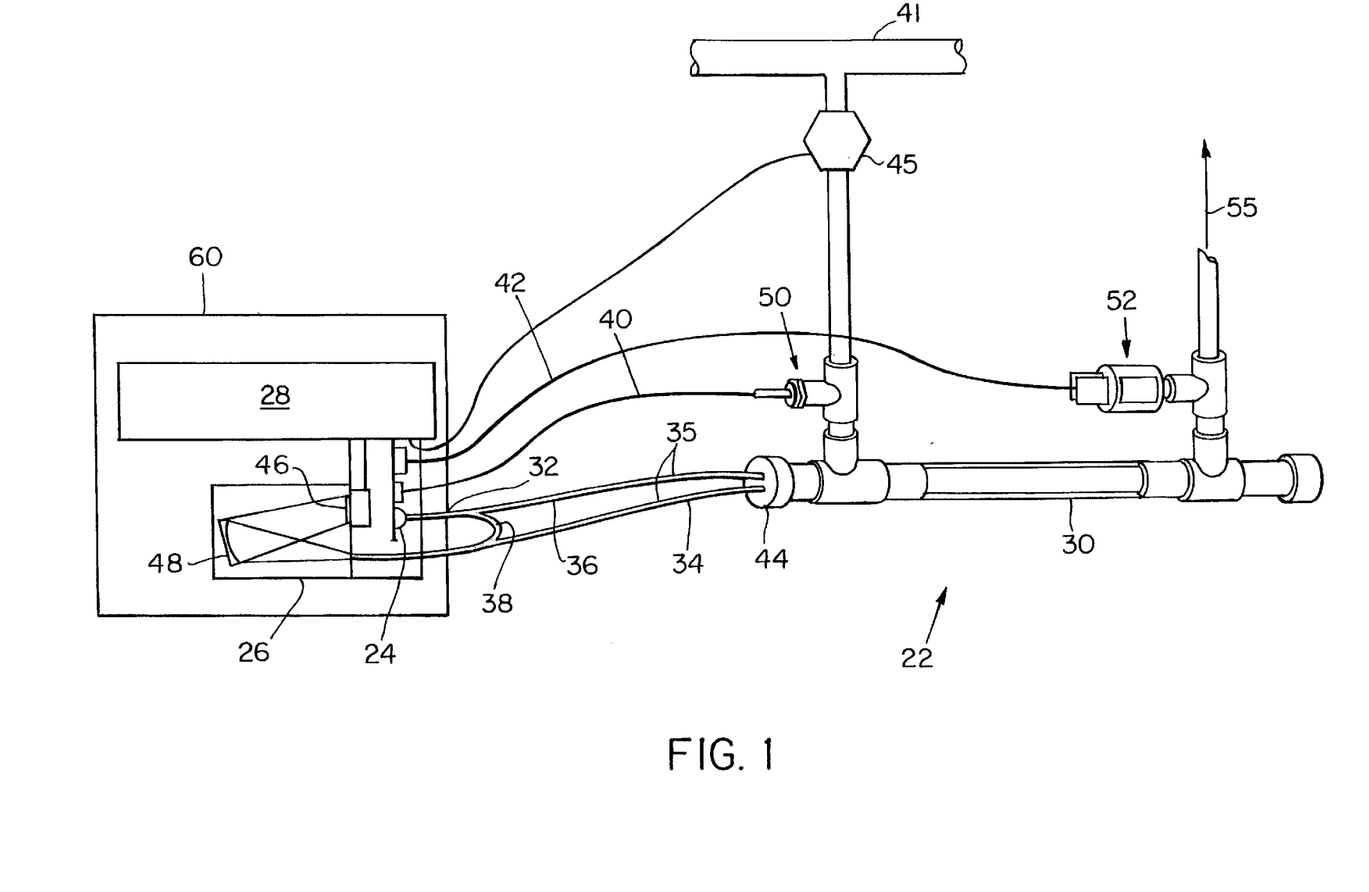
FIG. 1 is a schematic block diagram of a preferred embodiment of the present invention.

The sensor apparatus of the present invention is illustrated schematically in FIG. 1. In a preferred embodiment the sensor comprises two compact modules, an electronics module 20 and a sample module 22. The electronics module 20 includes a light source 24, a spectrograph 26, and electronics 28 preferably in an explosion resistant housing 60. The sample module 22 comprises a gas sample cell 30 that can also be included in housing 60. Fiber optics 32 optically link the sample module 22 to the electronics module 20. Natural gas is drawn from pipeline 41 into the cell 30. The gas flow can be automatically controlled from module 20 via valve 45, or may be separately controlled, or may be controlled passively, such as with a pressure regulator or a flow constrictor. The gas can be directed out of the cell 30 through outflow line 55 which can have a second valve and/or pump. Valve 45 can also be used to introduce a second gas for calibration or purging.

Light from the light source 24, preferably a near-visible light emitting diode (LED), is directed into the fiber optics 32. The fiber optics 32 can include two paths, a sample path 35 and a reference path 38. The sample path 35 directs the light into the sample cell 30, which preferably has an absorption path length in the range of 50–150 cm. The sample path 35 includes a transmission path 36 for transmitting light to the sample cell 30 and a return path 34 for returning the light transmitted through the sample, known as the sample beam, to the electronics module 20. The reference path 38 returns emitted light directly back into the electronics module 20 to serve as a reference beam alongside the sample beam.

A spectrograph 26 in the electronics module 20 processes the reference beam and sample beam. The spectrograph 26 preferably comprises a concave holographic grating 48 for dispersing the light and a CCD array 46 for detection of the dispersed light.

The sample and reference spectra, which fall on different portions of the array, are read out using the CCD array video electronics 46 and delivered to a microprocessor 28. The absorption spectrum of the sample is calculated from the ratio of the sample and reference spectra and a pre-recorded ratio for the cell 30 filled with a non-absorbing gas or evacuated. A fitting method processes the spectrum and determines the number densities of the distinguishable hydrocarbon components in the sample. This information is combined with temperature 40 and pressure 42 data, from which the sum of the non-absorbing species, typically $O_2$, $N_2$, $CO_2$, and He is inferred. The temperature data 40 are preferably collected at a temperature sensor such as a thermocouple or thermistor 50 at the input port of the cell 30 and the pressure data 42 are preferably collected at a pressure transducer 52 at the cell 30 output port. Sensor output preferably includes both the BTU content and chemical composition information including: mole fractions of methane, ethane, propane; total non-absorbing species; and combinations of the higher hydrocarbons.

The system of the present invention provides on-line, optically-based sensors for natural gas BTU content and chemical composition which can be installed in storage, transmission, and distribution facilities in a cost-effective manner. Due to the wide variation in chemical composition of natural gas, the measurements of BTU at all major custody transfer points is essential for effective natural gas utilization. The economic value of the natural gas is determined by the BTU content and the volume transferred. To ensure accurate pricing and protection of small profit margins, the BTU measurement accuracy is preferably within a tolerance of 1%. In addition, knowledge of the composition enables calculation of other properties such as compressibility, dew point and the Wobbe index.

The optically-based BTU and composition sensor of the present invention addresses this need by employing relatively inexpensive silicon CCD detector arrays and associated electronics. This low cost technology allows for the production of accurate, reliable sensors at a fraction of the initial and operating costs of current BTU-measuring systems. The reduced cost makes it feasible to install many more sensors, for example a sensor at each feed line in a distribution system, and therefore monitor the calorific value of the natural gas at various locations along the distribution chain with greater precision. This leads to greater efficiency in gas production and more uniform BTU content for the end user.

The measurement method of the present invention includes the step of first acquiring an absorption spectrum of a natural gas sample in a region around 900 nm using a broad-band light source and a small spectrograph having a silicon CCD array detector as shown in FIG. 1, described above. Following this, the spectrum is decomposed into distinguishable, known hydrocarbon component spectra. The component mole fractions or concentrations are calculated from the magnitudes of the component spectra with the aid of the temperature and pressure measurements, and the BTU value is calculated for the desired temperature and pressure condition using the mole fraction values.

At the preferred wavelengths and with the available spectrograph resolution the absorbance is essentially linear with the species number densities. It therefore follows that the spectra of hydrocarbon mixtures are the sum of the number density-weighted spectra of the pure species. Small corrections account for any deviation from linearity and for temperature-dependencies of the spectra.

A preferred method of analyzing the data can be described in the following manner.

The quantity to be measured, optical transmittance, is defined by the ratio of transmitted light intensities at a given wavelength over the same optical path with the sample present (I) and absent ($I_0$)

$$\tau = I/I_0 \quad (1)$$

In the sensor it is desired to measure $I_0$ as infrequently as possible. To compensate for fluctuations in light intensity, detector responsivity, etc. between $I_0$ measurements, a correction is applied based on the simultaneous measurement of a reference beam:

$$\tau = (I/I_0)/(R/R_0) \quad (2)$$

To eliminate the noise in $R/R_0$ while retaining the wavelength variation, $R/R_0$ can be replaced with a fit.

From the reference-corrected transmittance, the spectral absorbance, $A = -\ln(\tau)$, is calculated. According to Beer's law, which holds when the spectrum is unstructured on the scale of the instrument resolution, the absorbance at each wavelength is linearly related to the species number densities:

$$A = L \Sigma \sigma_i \rho_i \quad (3)$$

Here L is the path length, $\sigma_i$ and $\rho_i$ are respectively, the absorption coefficients and number densities of the species I, and $\Sigma$ denotes the sum over I. The number density is related to the pressure P and Kelvin temperature T via the non-ideal gas law, $$\rho RT = P/Z \quad (4)$$

where R is the gas constant and Z is the compressibility function evaluated for the pressure, temperature, and composition conditions.

Implicit in Eq. (3) is the assumption that the absorption coefficient for a given temperature does not depend on the number density (i.e., pressure). Accordingly, the determination of the sample composition (i.e., the $\rho_i$) and hence the BTU value is reduced to a decomposition of the absorbance spectrum into pure-species, spectra which have been separately measured. At the sample pressures Eq. (3) provides an accurate approximation for all natural gas components in the 819–980 nm region except methane. For methane, which has a somewhat structured spectrum, there is some dependence of the structure on number density; however, there is no measurable density-dependence of the integrated absorption coefficient (see below). As a result, even for methane the number densities derived using Eq. (3) are not very sensitive to the conditions under which the pure component spectrum is taken.

The BTU value of the sample per cubic foot at 60 F (15.6 C) and 1 atm (14.70 psi) is given in terms of the composition by $$\text{BTU Value} = 4.74 \Sigma X_i H_i / z_o \quad (5)$$

where $X_i = \rho_i/\rho_T$ are the species mole fractions, $H_i$ are the species heats of combustion in kcal/mole, $\rho_T$ is the total number density, and $Z_o$ is the compressibility at 60° F. and 1 atm. $\rho_T$ is calculated from the sample pressure using Eq. (4) rather than by simply summing the optically determined hydrocarbon species densities because of the likely presence of "inert" gases such as He, $N_2$, $O_2$ and $CO_2$.

The compressibility Z in Eq. (4) can be calculated from the measured pressure and temperature and the sample composition. With an unknown sample, an initial estimate of the hydrocarbon and total inert gas mole fractions can be made, then the Z value and species mole fractions can be iterated several times to converge the results.

The species number densities $\rho_i$ can be obtained from the sample spectrum via a standard linear regression (least-squares) fit to Eq. (3). To best fit the structured part of the spectrum, the pure methane reference spectrum measured at the nearest methane number density can be used. To eliminate residual baseline offsets which may be caused by optical misalignments associated with sample pressure transients, thermal expansion and refractive index changes, two alternate approaches can be employed. The first is to zero the average absorbance in the 816–830 nm region, where there is no appreciable absorption by any of the gas species. This approach can be used to generate accurate pure-species spectra. The second approach, which can be used in analyzing the mixed samples, is to include a baseline offset as an additional free parameter in the fit. The wavelength range of the fit can be 840–960 nm, corresponding to the approximate limits of the main absorption bands. However, very similar results are obtained by fitting to a smaller range of 850–950 nm.

A process for analyzing the data is illustrated in connection with the process flow sequences of FIGS. 7A–7D. The sample is measured, and the resulting spectrum (or spectra) is electronically stored in memory. The spectrum is decomposed or deconvoluted into densities $\rho_i$ of discrete components, regression and/or correction subroutines are performed and temperature dependence of the spectra is accounted for as needed. Mole fractions are determined by combining the $\rho_i$, the pressure measurement, and a compressibility calculation. The energy (BTU) content of the sample is then determined, and the composition and energy content are then displayed for the user, are recorded, or are forwarded from the remote collection site to a central site for further processing and storage.

Figure 7A:
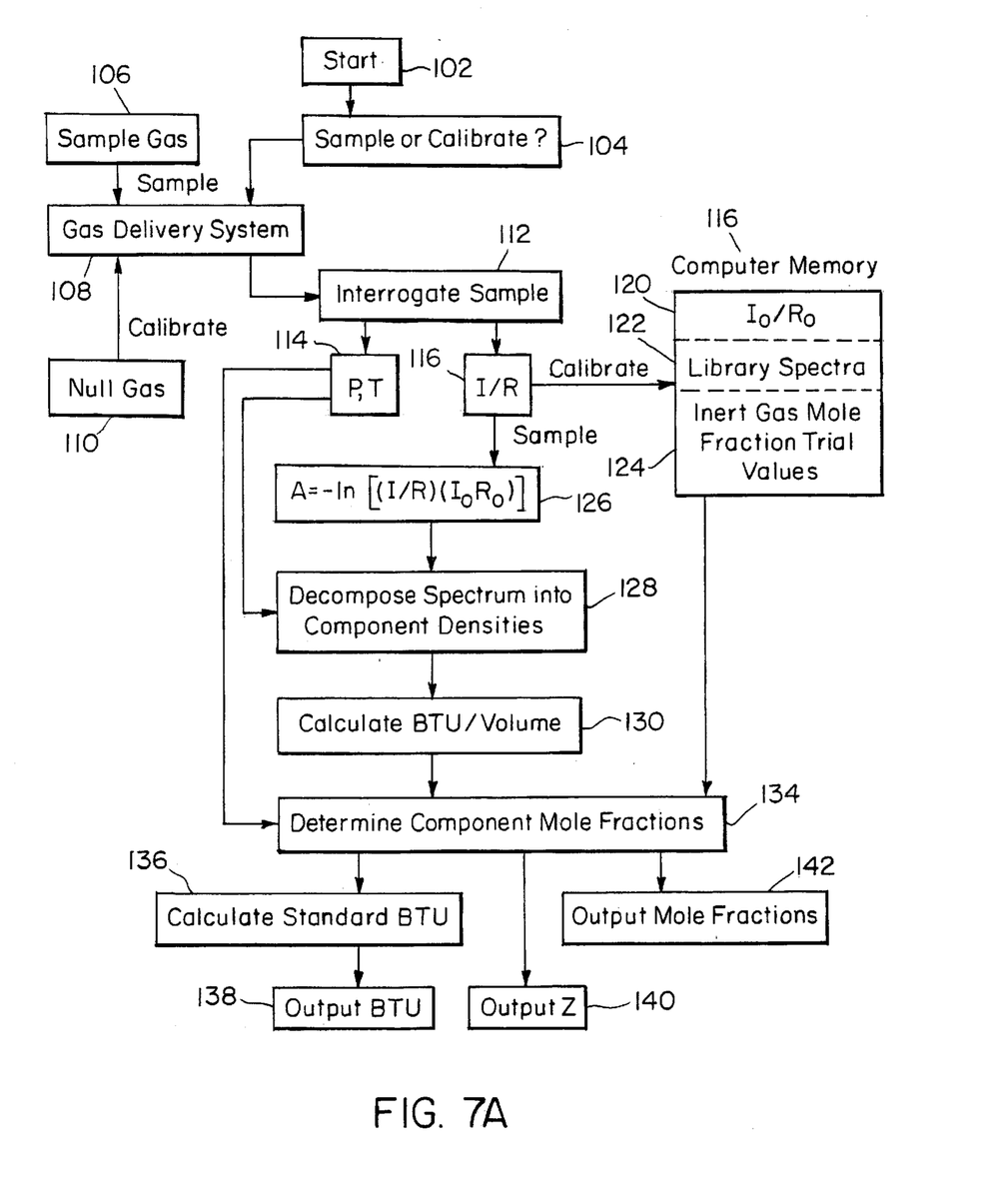
FIGS. 7A–7D are schematic diagrams of process flow sequences in accordance with the invention.

A process 100 for performing the measurement and analyzing the data is illustrated in FIG. 7A. The software is initiated 102 by the user or automated to periodically or continuously sample the fluid flow. The choice is made between operating the system in sample or calibrate mode 104. If sample mode is chosen, the pipeline gas sample 106 is introduced into the sample cell of the sensor by the gas delivery system 108; if calibrate mode is chosen, the null (calibration) gas 110 is chosen, which is preferably a non-absorbing gas as such as air. The gas is measured 112 by the sensor, resulting in the measurement of the pressure and temperature 114, and the ratio I/R 116 of the sample path to reference path spectra. In calibrate mode, this ratio is stored in the computer memory 118 as $I_0/R_0$ data 120. In sample mode this ratio is combined with the prestored $I_0/R_0$ to calculate the spectral absorbance A 126. The absorbance is then decomposed 128 into the hydrocarbon component densities $\rho_i$ using pre-stored library spectra 122 at different temperatures and pressures. If desired as an output, the BTU content per unit volume at the measurement pressure and temperature can then be computed 130. Next, the component mole fractions are calculated 134. This calculation makes use of a method for calculating the compressibility, Z, at the measurement temperature and pressure for a given hydrocarbon component and inert gas mole fractions. This method can include the use of a look-up table or formula derived from a survey of natural gas composition for estimating mole fraction values for each inert gas from the hydrocarbon component mole fractions, the total inert gas mole fraction, or other factors, and a process for calculating Z from these estimates. The Z calculation procedure is preferably the 1992 American Gas Association Report No. 8 method, which is incorporated herein by reference. The mole fractions are used to calculate 136 the BTU content under standard conditions, such as by using Eq. (5). The mole fraction composition 142, the BTU or thermal content 138, and the compressibility 140 are then displayed for the user, recorded, or forwarded to another site for further processing and storage.

Figure 7B:
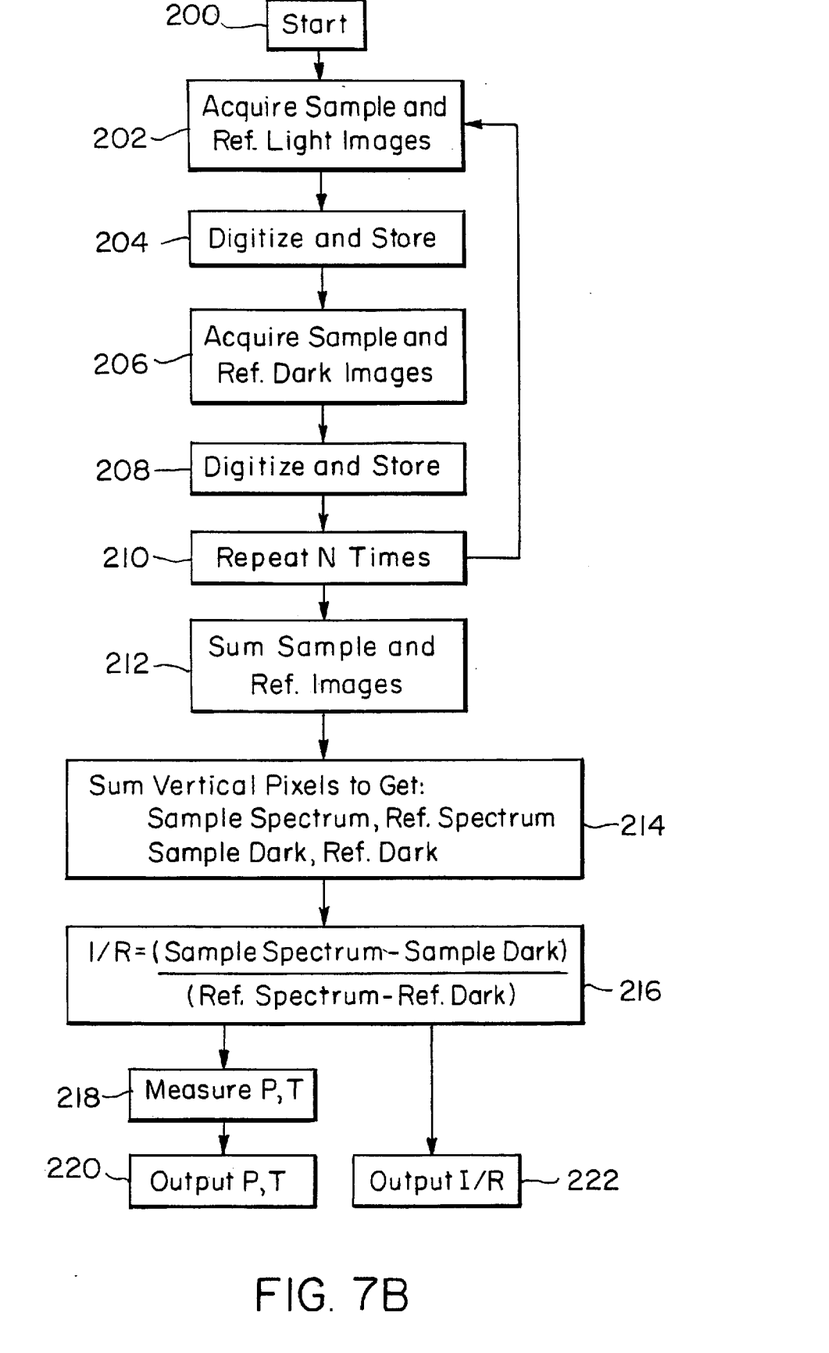

FIG. 7B illustrates in detail the method for measuring the sample initiated at 200. The silicon detector array exposures for the sample and reference light beams are acquired 202, digitized and stored 204 as images. The corresponding sample and reference dark exposures (i.e., with the light source turned off or blocked) are also acquired 206, digitized, and stored 208 as images. A preset number, N, of such exposures are performed 210 and are summed 212. If the detector arrays are 2-dimensional, for each image the readings from the pixels in the "vertical", dimension (defined to be the dimension perpendicular to the axis along which the wavelengths are dispersed) are summed 214, to yield the corresponding spectrum. The ratio I/R is calculated 216 from the ratio of the dark-spectrum-subtracted sample and reference spectra and output 222. The pressure P and temperature T in the sample cell are also measured 218 and output 220. In a preferred embodiment, the images to be summed are taken with differing exposure times, so as to maximize the signal to noise ratio and minimize the digitization bit noise.

Figure 7C:
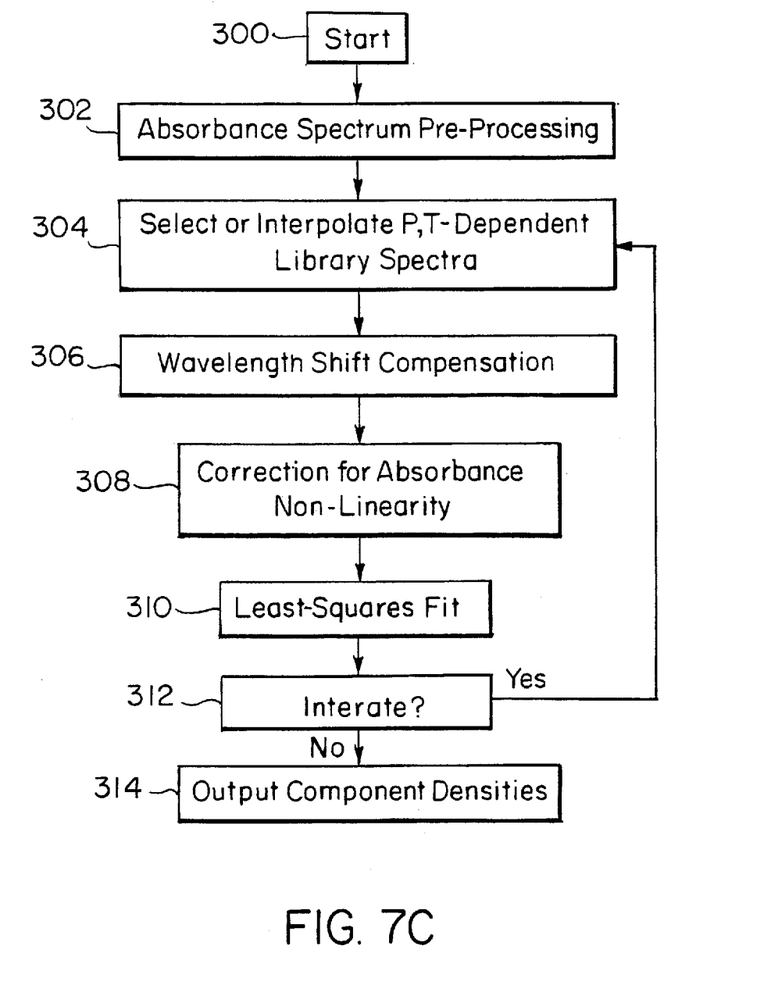

FIG. 7C illustrates in detail the method 300 for decomposing the spectrum into hydrocarbon component number densities. The absorbance spectrum can be pre-processed 302 by digital filtering, for example, to remove noise. Then the library spectra, which are tabulated for different temperatures and (at least for methane) pressures are selected or interpolated 304 based on the measured temperature and pressure. A method for compensating 306 for any wavelength shift of the spectrograph relative to a trial spectrum generated from the library is then applied. This method can consist of a routine which locates methane spectral peaks and/or valleys in the measured spectrum, compares them with the library spectra, determines the shift, and applies the shift to the library spectra. Alternatively, the method can generate a component, consisting of the difference between two spectra shifted in different directions, which is then passed on to the least-squares fit algorithm. Next, a correction 308 for absorbance non-linearity is applied if necessary. The resulting spectrum, the library spectra, and the optional difference spectrum are passed to a least-squares fitting routine 310 which extracts the hydrocarbon component number densities $\rho_i$. If the trial spectrum used in the wavelength shift compensation and non-linearity corrections is very different from the actual spectrum, it may be necessary to perform one or more iterations 312 of the wavelength-compensation, non-linearity correction, and least-squares fitting steps. The component densities are then stored 314.

In measurements performed with this invention, improvements in both the BTU and composition accuracy were obtained by adding a baseline slope as an additional component in the spectral fits. This slope is a residual that is not eliminated by applying the ($R/R_0$) correction factor in Eq. (2). Its physical origin in the apparatus can include small temperature gradients across the CCD array, which may affect the pixel gains and dark currents. Including the five distinguishable hydrocarbon spectra (methane, ethane, propane n-butane, and isobutane), the baseline offset and slope, and the shift-correction component, there are a total of eight variables in the least-squares fitting method.

Figure 7D:
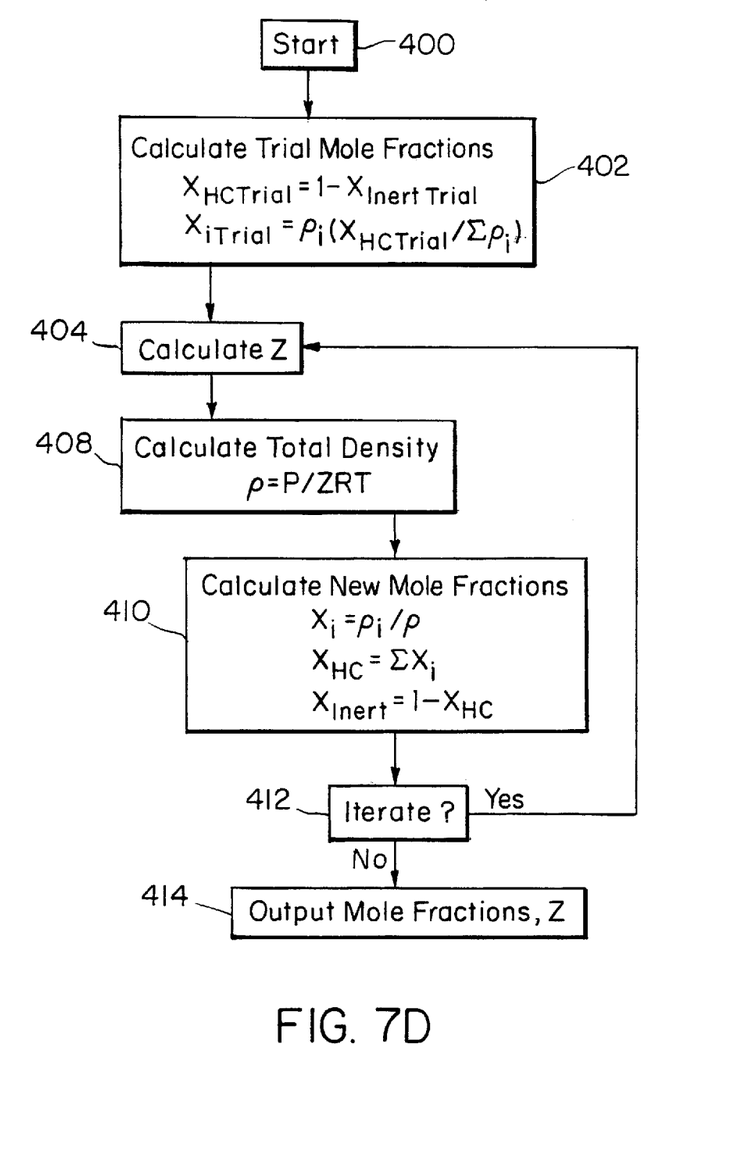

FIG. 7D illustrates in detail a method initiated at 400 for determining the component mole fractions. At trial mole fraction value for the total "inert" gases (124 in FIG. 7A) is combined with the trial hydrocarbon species mole fractions which are calculated 402 as indicated. The results are used to compute the compressibility 404. The result 406 is then used to calculate the total density, $\rho$ 408. Then, new mole fraction values are calculated 410 as shown. A decision on whether to iterate 412 the calculation of the compressibility and mole fractions is made based on the differences between the new and trial mole fraction values. The final mole fraction and compressibility values are then output 414.

Using the described invention, accurate spectral measurements of the pure hydrocarbon gases at high pressures have been performed. Absorption coefficients measured in the system are shown in FIGS. 2 through 6 for the five most abundant pure hydrocarbon vapor species in natural gas: methane, ethane, propane, n-butane, and isobutane. The coefficients have been divided by RT for use with species densities expressed as a compressibility-normalized pressure, $P/Z=\rho RT$, in units of atm or psi.

For all of the gases except methane, identical results are obtained at the different pressures, which range nearly up to the vapor pressure of each species at room temperature, to within the transmittance measurement accuracy of about 0.001. This indicates that for these pure species, Beer's law is closely observed.

Figure 2:
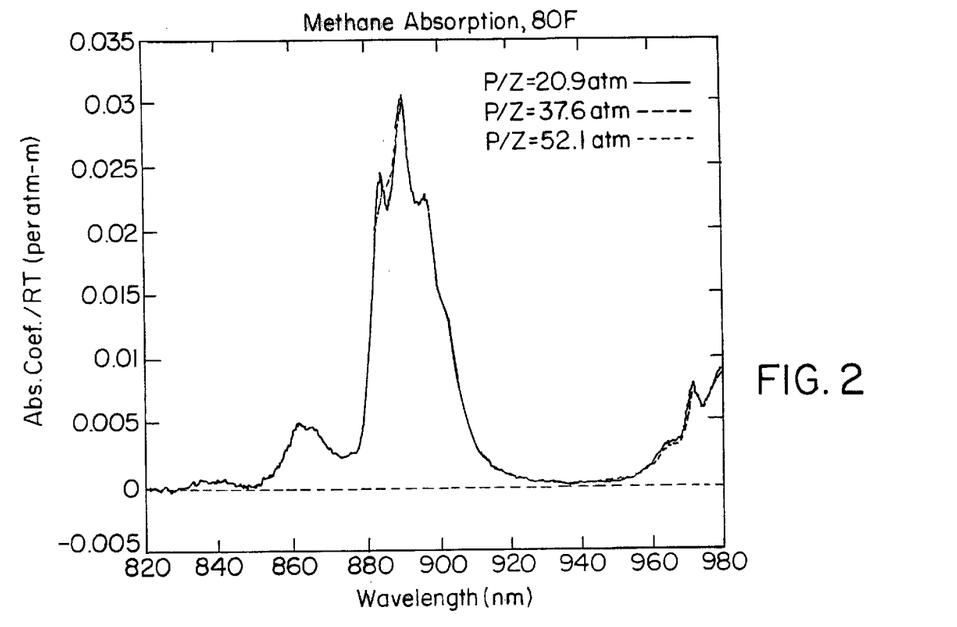
FIGS. 2–6 are graphical illustrations of absorption coefficients of methane, ethane, propane, n-butane and isobutane as a function of wavelength.
Figure 3:
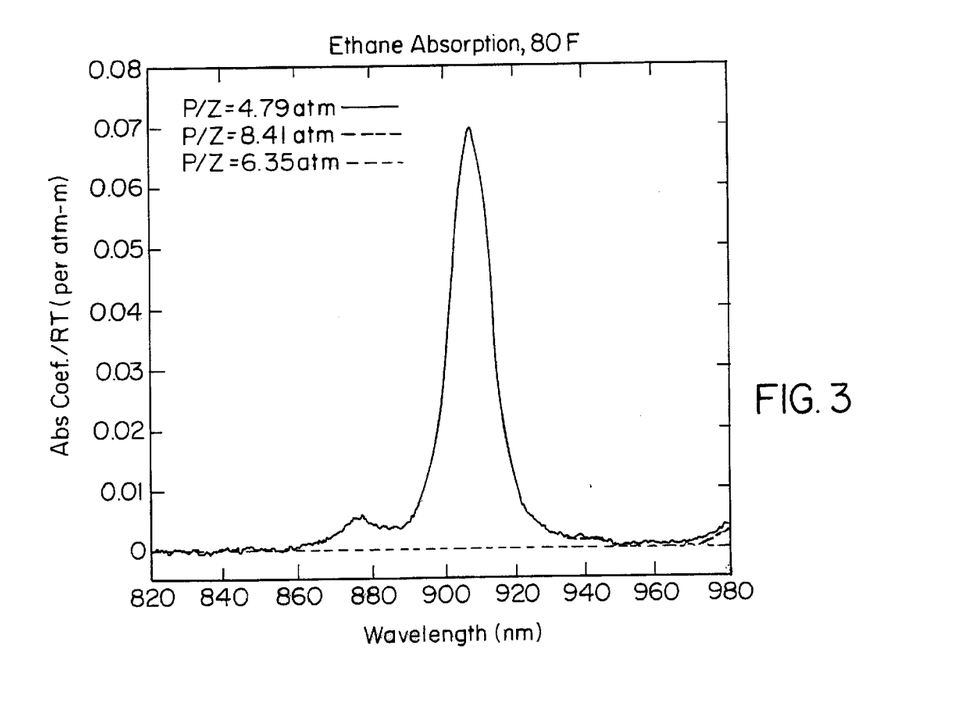
Figure 4:
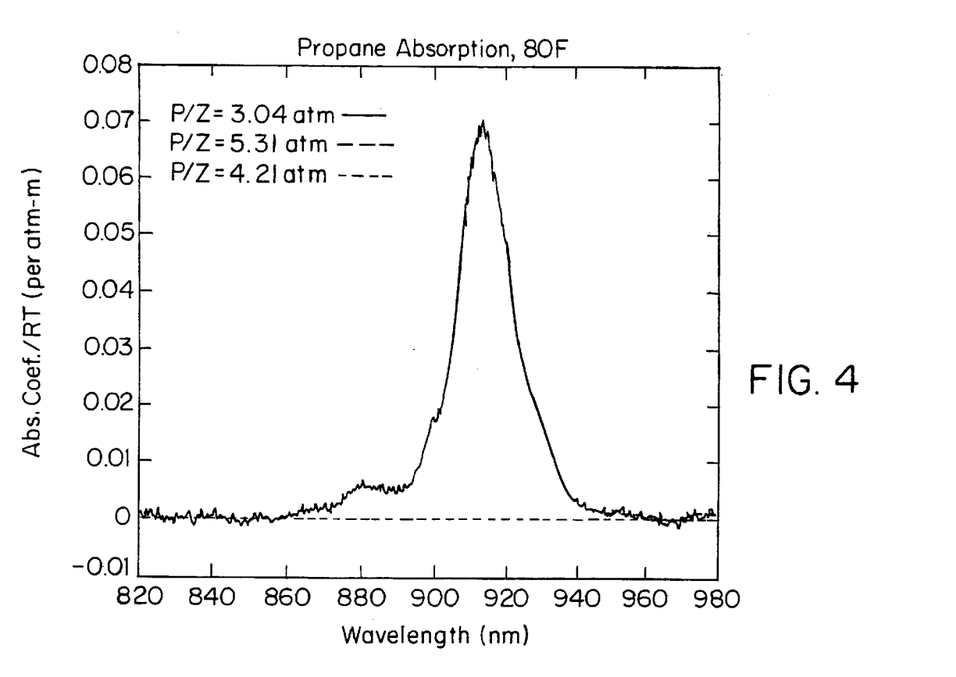
Figure 5:
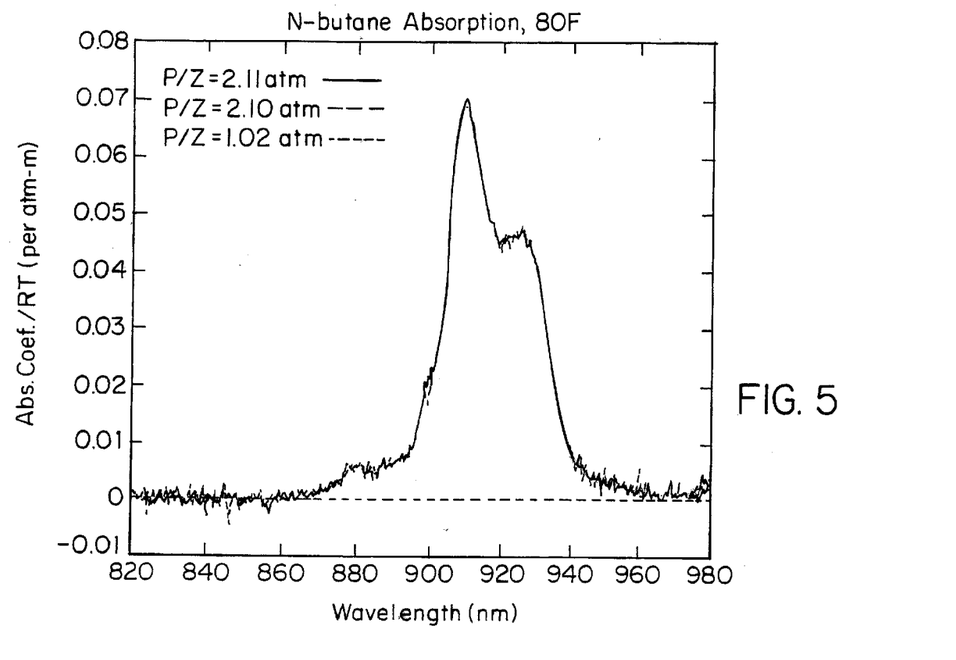
Figure 6:
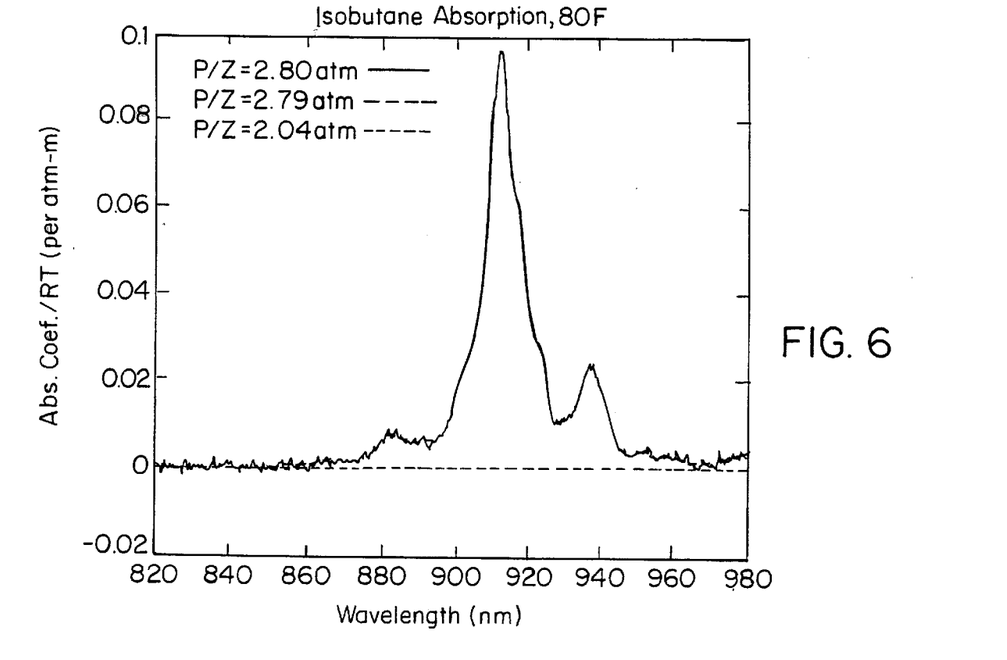

For methane there is a very small shift of absorption to higher wavelengths as well as smoothing of the structure at the center of the main band as the pressure is increased (see FIG. 2). However, over this pressure range no systematic variation in the integral of the absorption coefficient across the band is found to within the measurement precision, consistent with the conservation of oscillator strength.

The spectra of these five species are completely distinguishable from each other. The spectra of propane and the butanes differ from each other by virtue of their different numbers of the three molecular functional groups, $CH_3$; $CH_2$ CH, which absorb near 910 nm, 925 nm, and 935 nm, respectively. The methane and ethane spectra peak at lower wavelengths and are thus distinguishable from the higher hydrocarbons.

Figure 8:
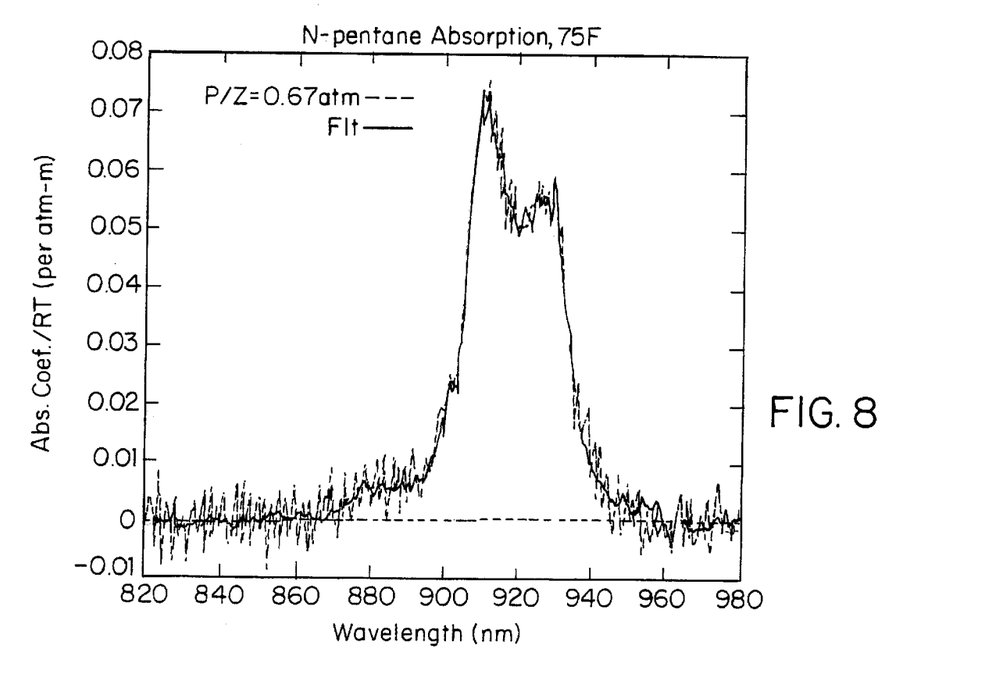
FIG. 8 is a graphical illustration of the absorption coefficient of N-pentane and a least squares fit in accordance with the invention.
Figure 9:
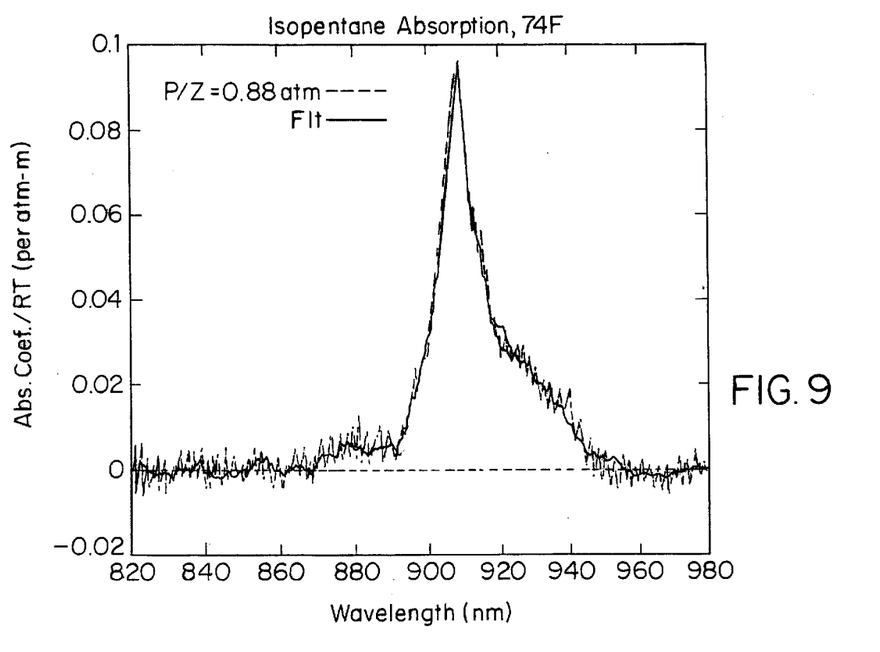
FIG. 9 is a graphical illustration of the absorption coefficient of isopentane and a least squares fit in accordance with the invention.

Spectra of n-pentane and isopentane, which are present in natural gas in small quantities (usually 1% or less), are shown in FIGS. 8 and 9. The relatively high noise levels are due to the subatmospheric pressures of the samples, which were close to the room-temperature equilibrium vapor pressures.

The pentanes contain the same functional groups as the five more abundant hydrocarbon species, and as a result their spectra cannot necessarily be distinguished from linear combinations of them. To illustrate this, least-squares fits of the pentane spectra were performed using the five abundant pure species spectra. The results are shown in FIGS. 8 and 9. Over virtually the entire wavelength range the fits agree with the data to within the noise level of the measurements. The combination coefficients of the fits are listed in Table 1 below along with their corresponding BTU values (i.e., the sum of the coefficient-weighted pure-species BTU's). The near-zero coefficients for methane indicate that methane remains completely distinguishable from the pentanes as well as from ethane, propane, and the butanes.

For n-pentane, the best-fit combination BTU value is 8% below the actual BTU value of about 4006, while for isopentane it is 16% below the actual BTU value of about 3998. Thus, for a gas sample containing pentane, these differences will result in an underestimation of the BTU derived from a spectral fit to methane, ethane, propane, n-butane, and isobutane components. However, the error scales with the pentane mole fraction, which is small. For example, for a sample containing 0.5% n-pentane and 0.5% isopentane, the net BTU measurement error is (0.005×0.08× 4006+0.005×0.16×3998=5 BTU, or 0.4% of a typical BTU value of 1250. For low-pentane samples, the error is much smaller. For higher hydrocarbons (hexanes, etc.), the BTU errors resulting from the use of the five-species bases set is negligible due to the very low concentrations of these species.

For both pentanes, the sum of the coefficients in Table 1 is within a few percent of unity. This means that for realistic pentane concentrations the total hydrocarbon mole fraction measured, from which the mole fraction of the "inert" gases is determined, is correct within a small margin of error described hereinafter.

TABLE 1

Coefficients of pentane spectra in terms of methane, ethane, propane, n-butane, and isobutane components. Values are averages of least-squares fits to three measurements

|  | Methane | Ethane | Propane | N-butane | Total | BTU |
|---|---|---|---|---|---|---|
| N-pentane | −0.007 | −0.154 | −0.180 | 0.045 | 1.021 | 3690 |
| Isopentane | −0.053 | 0.309 | −0.241 | 0.542 | 1.082 | 3347 |

The above spectral measurements indicate that the number of distinguishable spectral components that can be extracted from the sample spectrum, typically five, is fewer than the total number of hydrocarbon species that may be present in natural gas. Therefore, there is some ambiguity in the derived composition. However, the BTU value can still be calculated accurately as long as there is a direct correspondence between the spectrum and the BTU. Such a correspondence is indicated by observations that: (1) the spectra of the non-methane hydrocarbons can be approximated as sums of spectra of the three molecular functional groups, CH, $CH_2$, $CH_3$; and (2) the hydrocarbon BTU values can be accurately represented as a sum of the functional group BTUs. Due to a wavelength shift of the $CH_3$ group in ethane compared with the higher hydrocarbons, a fifth spectral component can also be distinguished. Since linear combinations can be taken, an arbitrary basis set can be constructed from these components. An example of the basis set is the spectra of methane, ethane, and the CH, $CH_2$, and $CH_3$ groups.

The basis components can alternatively be considered to be the spectra of the five most abundant hydrocarbons, which are methane, ethane, propane, n-butane, and isobutane. With this basis set, the pentane and higher hydrocarbon number densities are expressed as linear combinations of ethane, propane, and the butanes (the methane coefficients are close to zero). This approach is more convenient than using the functional group basis set, since it directly yields an "effective" hydrocarbon composition, from which one can accurately calculate the sample compressibility. An alternative basis set, which produces virtually identical compressibilities and BTUs but more realistic number densities for the higher hydrocarbons, can consist of the spectra of methane, ethane, propane, a combination of the higher linear hydrocarbons in specified relative proportions, and a combination of the higher branched hydrocarbons in specified relative proportions.

The sample BTU, or thermal content, value is calculated by summing the BTUs for the five basis species weighted by the measured mole fractions. The BTU values for the linear combinations that represent the pentanes are comparable to the actual BTU's, and similar results occur for the higher hydrocarbons. For natural gas samples, the best overall accuracy using the pure hydrocarbon basis set is achieved by small, empirical adjustment (by several percent) of the BTU values assigned to the n-butane and isobutane spectral components.

Since the methane spectrum is completely separable from those of all other species, and the total hydrocarbon number density is accurately calculated using a five component basis set, both the methane and the "inert" gas mole fractions can be provided with an accuracy comparable to that of the BTU value. For the other hydrocarbons, the mole fraction accuracy will depend on the choice of basis set, and is estimated to be in the 0.10% mole fraction range.

An experiment was conducted for BTU and composition measurements using the apparatus and method of the present invention. The experiment covered three different hydrocarbon mixtures over a wide range of number densities. The results are summarized in Table 2. The number densities are listed as P/Z, where P represents pressure and Z represents compressibility. The values are based on linear regression fitting using pure-hydrocarbon basis functions. Note that corrections for possible absorbance nonlinearity or pressure measurement errors have not been made.

TABLE 2

Summary of BTU and Composition Measurements

| Sample Mixture | BTU Value | P/Z Range (psi) | Mole Fraction Accuracy[a] | Mean BTU Accuracy | BTU Precision |
|---|---|---|---|---|---|
| methane + ethane | 1089[b] | 330–782 | 0.006 | 0.3% | 0.4% |
| methane + ethane + propane + n-butane | 1191[b] | 248–904 | [c] | [d] | 0.5% |
| GPA Reference | 1296[e] | 192–218 | 0.005 | 0.8% | 0.3% |

Figure 10A:
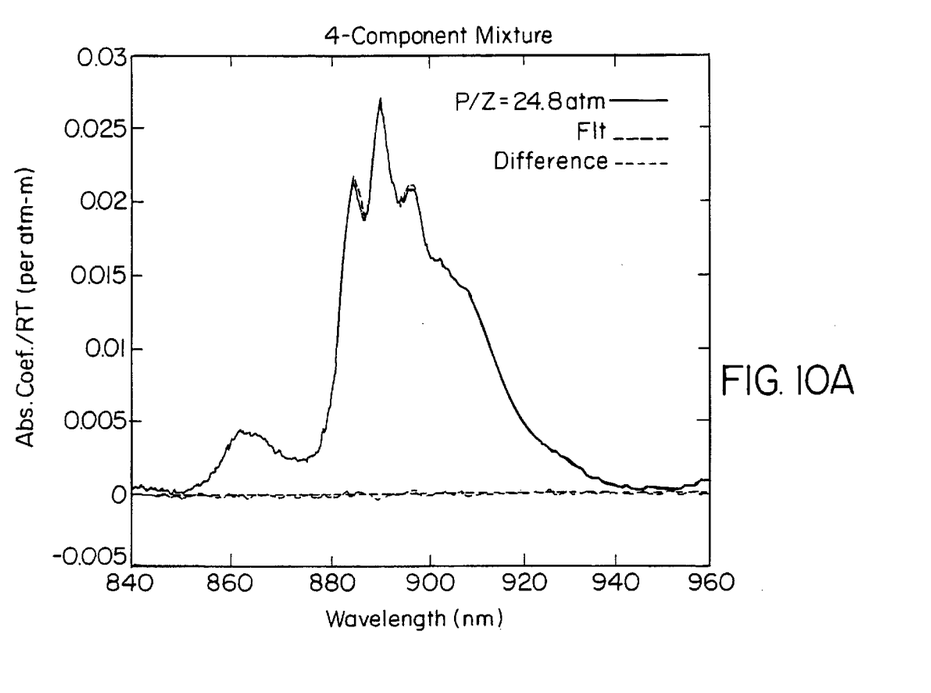
FIG. 10A graphically illustrates results for an experiment conducted in accordance with the apparatus and method of the present invention.

[a]-Range of all measurements
[b]-Calculated from sample preparation procedure
[c]-0.012 including sample preparation uncertainty
[d]-1.1% including sample preparation uncertainty
[e]-Composition certified by GC analysis One example of a measured spectrum and the least-squares fit is shown in FIG. 10A. Above around 30 atm pressure, the data vs.-fit differences are almost entirely in the structured part of the methane band. At lower pressures, this part of the spectrum is more accurately fit, which tends to make the overall error smaller despite some loss of signal-to-noise due to the smaller absorption. The absorption can be increased by using a longer optical path, which further improves the measurement accuracy.

Table 3 shows the results for a binary mixture of 89.5% methane and 10.5% ethane (BTU value=1089) which was prepared by combining known pressures of the two gases in the same measurement cell. The mixture was prepared at a total pressure of 700 psi (P/Z=782 psi or 48 atm at 74 F) and allowed to equilibrate overnight; then measurements were made at a series of pressures down to 315 psi as the cell was pumped out.

TABLE 3

Results from optical measurements on a prepared 89.5% methane/10.5% ethane mixture

| P/Z (psi) | Mole Fractions | | | BTU Value |
|---|---|---|---|---|
| | Methane | Ethane | Total | |
| 782 | 0.890–0891[a] | 0.102–0.103[a] | 0.996–0.997[a] | 1087[a] |
| 690 | 0.894 | 0.104 | 1.000 | 1090 |
| 569 | 0.889 | 0.104 | 0.994 | 1082 |
| 450 | 0.890–0892[b] | 0.102–0.104[b] | 0.996–1001[b] | 1085–1086[b] |
| 330 | 0.901 | 0.100 | 1.001 | 1085 |
| Prepared | 0.895 | 0.105 | 1.000 | 1089 |

[a]Range of three measurements.
[b]Depending on pressure of methane component in fit.

The optically measured BTU values are seen to be in excellent absolute agreement (within an average of –0.3%) with that calculated from the preparation procedure. The measurement precision is ±0.4%. The mole fraction accuracy and precision are similar to these values. The former is well within the accuracy of the sample reparation, while the latter is consistent with a transmittance measurement precision of about 0.001.

Table 4 shows the results for a four-component mixture of methane, ethane, propane, and n-butane which was prepared by successively adding the pure gases to the sample cell in the reverse order. Nearly identical mole fractions and BTU values, to within ±0.5% precision, were obtained at pressures of P/Z=248–904 psi (17–61 atm) as the cell was pumped down. This confirms the close adherence of the absorption to Beer's law for this complex mixture as well as for the-pure components. The difference between the average optically measured BTU value and the value calculated from the gas preparation procedure, 1191 BTU, is +1.1%. The optically measured species mole fractions agree with the "prepared" values to within 0.01 for propane and methane and within 0.004 or better for ethane and n-butane. For this particular sample, most of the difference between the measured and "prepared" composition (and therefore the BTU value) may be due to gas preparation error rather than optical measurement error.

TABLE 4

Results from optical measurements on a prepared four-component mixture

| P/Z (psi) | Mole Fractions | | | | | BTU Value |
|---|---|---|---|---|---|---|
| | Methane | Ethane | Propane | N-butane | Total | |
| 904 | 0.851 | 0.072 | 0.048 | 0.028 | 1.001 | 1206 |
| 903 | 0.851 | 0.070 | 0.049 | 0.029 | 1.001 | 1205 |
| 697 | 0.848 | 0.071 | 0.048 | 0.029 | 0.997 | 1199 |
| 528 | 0.847 | 0.072 | 0.044 | 0.032 | 0.997 | 1204 |
| 364 | 0.854 | 0.072 | 0.043 | 0.032 | 1.002 | 1202 |
| 248 | 0.853 | 0.072 | 0.038 | 0.035 | 1.002 | 1211 |
| Prepared | 0.859 | 0.072 | 0.037 | 0.032 | 1.000 | 1191 |

Measurements have been conducted on a sample of GPA Reference Certified Master Gas. Three separate measurements at close to the cylinder pressure of around 200 psi were taken over a two-hour time span. The results are reported in Table 5. Due to the relatively low pressure, the measurement precision was expected to be somewhat poorer than with the in-house mixtures.

TABLE 5

Results from optical measurements on the GPA Reference Certified Master Gas

| P/Z (psi) | Mole Fractions | | | | | BTU Value |
|---|---|---|---|---|---|---|
| | Methane | Ethane | Propane | N-butane | Isobutane | |
| 200. | 0.701 | 0.090 | 0.054 | 0.046 | 0.041 | 1282 |
| 192. | 0.704 | 0.087 | 0.052 | 0.045 | 0.041 | 1273 |
| 218. | 0.708 | 0.086 | 0.057 | 0.043 | 0.039 | 1275 |
| Actual effective | 0.704 | 0.092 | 0.056 | 0.048 | 0.036 | 1286 |

The sample composition reported by the supplier is 70.41% methane, 9.00% ethane, 6.01% propane, 3.00% n-butane, 3.00% isobutane, 1.01% n-pentane, 5.02% $N_2$, 1.04% $CO_2$, and 0.50% He. The optical analysis reports the pentanes in terms of other components; the "actual effective" mole fractions and BTU value in Table 4 assume that the pentanes are represented as the linear combinations given in Table 2. The differences between these values and the measured ones are due to measurement errors.

Comparing the measured and "actual effective" values, the average BTU error is –0.7%, the precision is ±0.3%, and the mole fraction errors are 0.005 or less. These very good results compare quite favorably with the higher-pressure measurements on our in-house gas mixtures.

The true BTU value for a natural gas sample is approached by replacing the n-butane and isobutane BTU values with empirically adjusted ones. The result is an average measured BTU value of 1286. This is 0.8% below the actual value of 1296.

The main sources of error in this measurement are transmittance measurement error and pressure measurement error. According to the following analysis for a given optical path length and a sample pressure of around 200 psi, the BTU error associated with the transmittance measurement accuracy is about 0.5%. The slightly larger observed errors are not surprising when the pressure measurement accuracy is considered. According to the specification of our 1000 psig gauge, the pressure measurement is accurate to within 1.5 psi, or 0.7% of the sample pressure.

The sources of error in the optical BTU measurement can be divided into (1) systematic errors that can be compensated by calibration of the sensor with reference gases, and (2) other errors inherent in the technique. Compensatable errors amount to less than 1% of the BTU value. They include measurement errors associated with the pure species spectra, possible deviations from Beer's law, and pressure gauge inaccuracy. The latter two errors are not expected to be sensitive to the sample composition, and all of them can be compensated by calibrating the sensor using one or two known BTU gas mixtures. The pressure measurement accuracy can be improved by proper selection of the gauge to match the range of sample pressures. The selection of the preferred sample pressure is discussed below. The remaining sources of error determine the ultimate performance of the sensor. They include:

1. Transmittance measurement precision;
2. Hydrocarbon composition ambiguity; and
3. Inert gas composition ambiguity.

Each of these error sources are discussed briefly below, and the total anticipated measurement error is calculated.

The transmittance measurement precision, denoted $d_\tau$, can be estimated to be approximately 0.001. Applying the transmittance precision to the peak of the spectrum, the absorbance error is calculated using Beer's law, and the percent BTU measurement error is set equal to the percent concentration error. The result is $$\text{Percent BTU error} = 100 \, d_r \exp(A)/A \qquad 5$$

where A is the peak absorbance, which is proportional to the optical path length and sample pressure.

Figure 10B:
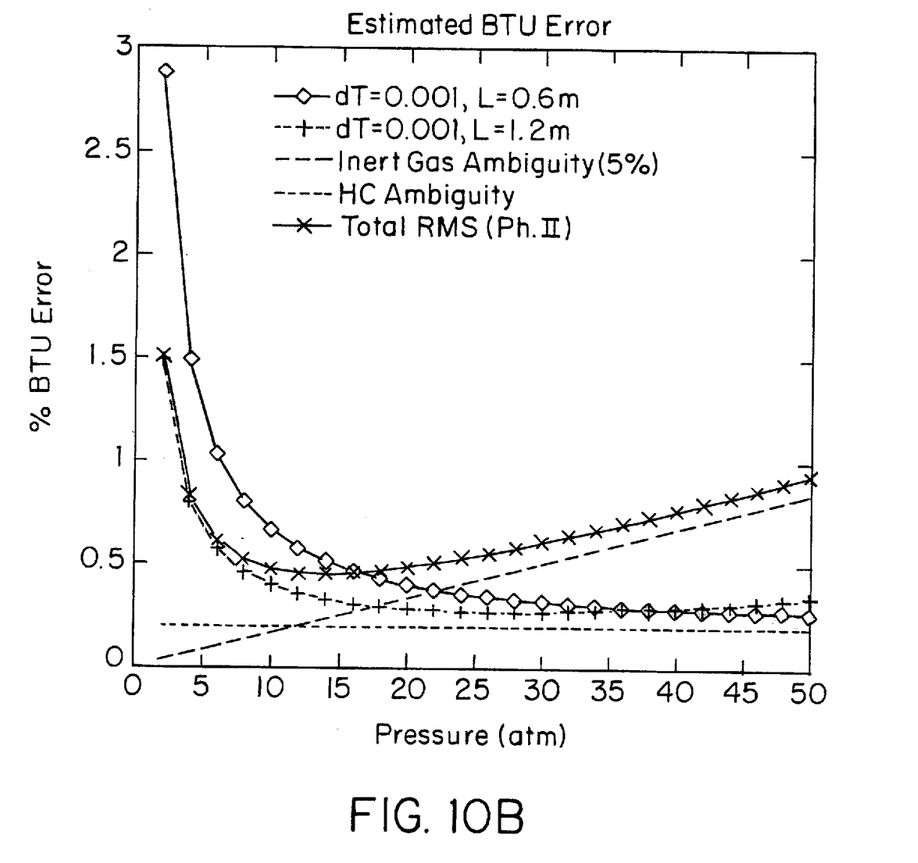
FIG. 10B graphically illustrates estimated BTU measurement errors.

The error is plotted as a function of sample pressure in FIG. 10B for two different path lengths, 0.6 m and 1.2 m; the peak absorption coefficient for a mostly-methane sample is assumed. The error estimated for the shorter path with pressures above 14 atm (around 200 psi) is 0.5% and is consistent with measurements on the binary and Certified Master Gas mixtures. With the longer path, the error is reduced except at very high pressures.

Hydrocarbon ambiguity error refers to the BTU error associated with the presence of n>4 hydrocarbons which are not directly measured but are instead subsumed under the other components. We, can roughly estimate this error based on (1) zeroing the BTU error for the mean pentane/butane ratio of about 1:3 by adjusting the n-butane and isobutane BTU's as discussed in Section 2.3, (2) assuming a maximum 50% deviation from this ratio over the range of natural gas samples, and (3) assuming a maximum 1.5% total concentration of butanes. The resulting fractional BTU error is 0.1%.

In addition to the hydrocarbons which are being measured, natural gas contains small amounts of other, "inert" gases, chiefly $N_2$, $CO_2$, and He. Although these gases have no heat content, they do affect the compressibility, Z, which enters into the BTU calculation through Eq. (4). Different assumptions about their proportions lead to slightly different Z values, which in turn lead to slightly different calculated number densities at the pressure to which the BTU value is referenced.

Based on a survey of typical natural gas compositions, one can estimate that the worst-case uncertainty in Z is approximately ±0.01% per atm of the difference between the measurement pressure and the BTU reference pressure. Assuming that the BTU reference pressure is 1 atm, the BTU uncertainty is shown by the dashed line in FIG. 10B. For better accuracy, an auxiliary measurement of the $CO_2$ or specific gravity can be included. If the BTU value is to be referenced to the pressure of the measurement, there is no error due to Z uncertainty.

The projected total BTU measurement error is approximated as the RMS sum of the above three independent errors. The projection is shown in FIG. 10B and it indicates that the optimum performance can be obtained at sample pressures of 15–25 atm (220–368 psi). Here, the error is 0.3%, matching the capability of the best on-line GC instruments. A worst-case estimate of the total error is given by the direct sum of the errors, which is 0.6%. This is still well within the performance target of less than 1%. Table 6 summarizes the error analysis at 14 atm.

TABLE 6

| BTU Error Analysis for Operation at 20 atm (294 psi) Pressure | |
|---|---|
| Source of Error | Estimated Value |
| Transmittance Uncertainty | |
| (0.6 m path) | 0.4% |
| (1.2 m path) | 0.3% |
| Hydrocarbon Ambiguity | 0.1% |

TABLE 6-continued

| BTU Error Analysis for Operation at 20 atm (294 psi) Pressure | |
|---|---|
| Source of Error | Estimated Value |
| Inert Gas Ambiguity | 0.2% |
| Net Error (1.2 m path) | |
| Worst-Case (Direct Sum) | 0.6% |
| Probable (Total RMS) | 0.3% |

While this invention has been particularly shown and described with references to preferred embodiments thereof, it will be understood by those skilled in the art that various changes in form and detail may be made therein without departing from the spirit and scope of the invention as defined by the appended claims.

We claim:

1. A system for measuring properties of a hydrocarbon fuel gas comprising:
    a light source generating light over a wavelength range;
    a pipe having a hydrocarbon fuel gas flow;
    a cell in fluid communication with the gas in the pipe such that gas located in the cell is optically coupled to the light source, the light being partially transmitted by the gas;
    a spectrograph that is optically coupled to the cell and that disperses the transmitted light;
    calibrating means for calibrating the spectrograph, the spectrograph having a resolution such that the calibration means calibrates a wavelength scale of the spectrograph;
    a silicon sensor array that detects at least some portion of the dispersed light in the range between 700–1000 nm and generates spectral data; and
    a processing circuit that processes the spectral data to determine a property of the gas.

2. The system of claim 1 wherein the properties comprise energy content and composition of the gas in the cell.

3. The system of claim 1 wherein the silicon sensor array comprises a charge coupled device (CCD).

4. The system of claim 1 wherein the silicon sensor array comprises a two-dimensional array.

5. The system of claim 1 wherein the light generated by the source is divided into a measurement beam for transmission to the natural gas in the cell and a reference beam, both beams being received by the spectrograph and detected by the silicon sensor array.

6. The system of claim 1 wherein the light source is a light emitting diode.

7. The system of claim 1 wherein the light source comprises a plurality of light emitting diodes that generates light over a wavelength range.

8. The system of claim 1 wherein the light source comprises an incandescent lamp.

9. The system of claim 1 wherein hydrocarbon fuel gas comprises natural gas.

10. The system of claim 1 further comprising a housing enclosing the sensor, the spectrograph and the processing circuit.

11. The system of claim 1 further comprising a plurality of sensors, each sensor coupled to one of a plurality of cells.

12. The system of claim 1 further comprising a fiber optic device that optically couples the light source to the cell.

13. The system of claim 1 further comprising a fiber optic device that optically couples the cell to the spectrograph.

14. The system of claim 1 further comprising a temperature sensor that measures the temperature of the gas in the cell.

15. The system of claim 1 further comprising a pressure sensor that measures a pressure of the gas in the cell.

16. The system of claim 1 wherein the processing circuit comprises a computer or microprocessor.

17. The system of claim 5 wherein the reference beam and measurement beam received by the spectrograph are detected on different portions of the silicon sensor array.

18. A method for determining properties of a hydrocarbon fuel gas comprising the steps of:
   acquiring an absorption spectrum in a region between 700 and 1000 nm of a hydrocarbon fuel gas, by irradiating the gas with a light source and by dispersing light transmitted through the gas with a spectrograph;
   detecting the dispersed light with a silicon sensor array;
   determining an absorbance spectrum of the gas;
   decomposing the spectrum into a plurality of hydrocarbon components; and
   determining properties of the gas from the components.

19. The method of claim 18 wherein the hydrocarbon fuel gas comprises natural gas.

20. The method of claim 18 wherein the step of determining further comprises the step of determining sample composition.

21. The method of claim 18 further comprising measuring the temperature and pressure of the gas.

22. The method of claim 18 wherein the step of acquiring further comprises the step of analyzing the transmitted light at a sensor comprising a charge coupled device (CCD) array.

23. The method of claim 18 further comprising determining an energy content of the gas.

24. The method of claim 23 wherein the step of determining the energy content comprises determining properties at a first state of pressure and temperature of the gas and determining energy content at a second state of pressure and temperature of the gas using the properties at the first state.

25. The method of claim 18 further comprising providing a two-dimensional silicon sensor array that detects the dispersed light.

26. The method of claim 18 wherein the step of determining the absorbance of the sample comprises comparing the absorption spectrum of the gas with reference data.

27. The method of claim 26 further including the step of obtaining the reference data which comprises coupling light from the light source to the spectrograph without transmitting the light through the cell.

28. The method of claim 18 further comprising storing library spectral data in a memory of a computer such that the library spectral data can be compared with the absorbance spectrum of the gas.

29. The method of claim 18 further comprising determining a compressibility value of the gas.

30. The method of claim 28 further comprising the step of decomposing the spectral data by calculating a wavelength scale of the data using library spectra.

31. The method of claim 18 determining the relative concentrations or mole fractions of a plurality of gaseous materials in the sample.

32. The method of claim 27 wherein the absorption spectrum and reference data are acquired from different portions of the silicon sensor array.

33. An optical system for measuring energy content and other proper ties of a natural gas comprising:
   a light source generating light over a range of wavelengths to provide a measurement light beam and a reference light beam;
   a pipe having a natural gas flow at a gas pressure above one atmosphere;
   a fixed optical path in fluid communication with the natural gas in the pipe such that natural gas in the optical path is optically coupled to the measurement light beam, the light being partially transmitted by the natural gas;
   a temperature sensor that measures a temperature of the natural gas;
   a pressure sensor that measures the gas pressure of the natural gas;
   a spectrograph that receives the measurement light beam that is transmitted by the natural gas and the reference light beam, the spectrograph dispersing the measurement and reference light beams onto a silicon sensor array that detects at least some portion of the light in the range between 700–1000 nm and generates spectral data,
   calibration means that calibrates the spectrograph using spectral features from the spectral data, the spectrograph having a wavelength resolution such that a wavelength scale of the spectrograph can be calibrated using the spectral features; and
   a processing circuit that processes the spectral data to determine the energy content of the natural gas.

34. The system of claim 33 wherein the silicon sensor array comprises a charge coupled device (CCD).

35. The system of claim 33 wherein the silicon sensor array comprises a CMOS device.

36. The system of claim 33 wherein the silicon sensor array comprises a charge-injection device (CID).

37. The system of claim 33 wherein the silicon sensor array comprises a photodiode array.

38. The system of claim 33 wherein the silicon sensor array comprises a two-dimensional array.

39. The system of claim 33 wherein the light source is a light emitting diode.

40. The system of claim 33 further comprising a metal explosion resistant housing enclosing the sensor and the spectrograph.

41. The system of claim 33 further comprising a fiber optic device that optically couples the fixed optical path to the spectrograph.

42. The system of claim 33 wherein the processing circuit comprises a computer or microprocessor.

43. The system of claim 33 further comprising a fiber optic device that optically couples the light source to the fixed optical path.

44. The system of claim 33 wherein the reference light beam and measurement light beam received by the spectrograph are detected on different portions of the silicon sensor array.

45. A method for determining the energy content and other properties of a natural gas comprising the steps of:
   acquiring an absorption spectrum of the natural gas by irradiating the gas with a light source and by dispersing light transmitted through the gas with a spectrograph;
   detecting at least some portion of the light in the range between 700–1000 nm with a silicon sensor array;
   determining the absorbance spectrum of the natural gas by comparing the spectrum of light transmitted through the gas with a reference spectrum obtained by coupling light from the light source to the spectrograph without transmitting the light through the gas;
   calibrating a wavelength scale of the spectrograph using spectral features of the natural gas;

decomposing the absorbance spectrum into a plurality of spectral elements corresponding to hydrocarbon components of the natural gas;

measuring the temperature and pressure of the natural gas;

determining the hydrocarbon composition of the natural gas from the decomposed spectral elements and the temperature and pressure data;

determining the energy content of the natural gas at a state of pressure and temperature using the determined hydrocarbon composition.

46. The method of claim 45 wherein the state of pressure and temperature at which the energy content is determined is different from the measured state of pressure and temperature of the natural gas.

47. The method of claim 45 further comprising determining the sum of the relative concentrations or mole fractions of the non-hydrocarbon gases in the natural gas.

48. The method of claim 45 further comprising storing library spectral data in a memory of a computer such that the library data can be compared with the absorbance spectrum of the natural gas.

49. The method of claim 45 further comprising determining a compressibility value of the natural gas.

50. The method of claim 45 further comprising providing a two-dimensional sensor array that detects the dispersed light.

51. The method of claim 45 wherein the spectrum of light transmitted through the natural gas and the reference spectrum are determined from different portions of the silicon sensor array.

52. A method for determining properties of a hydrocarbon fuel gas comprising the steps of:

acquiring an absorption spectrum in a region between 700 and 1000 nm of a hydrocarbon fuel gas at a line measurement pressure above one atmosphere, by irradiating the gas with a light source and by dispersing light transmitted through the gas with a spectrograph;

detecting the dispersed light with a silicon sensor array;

determining an absorbance spectrum of the gas; and determining energy content per unit volume at about the measurement pressure above one atmosphere.

53. The method of claim 52 wherein the hydrocarbon fuel gas comprises natural gas.

54. The method of claim 52 wherein the step of determining further comprises the step of determining sample composition.

55. The method of claim 52 further comprising measuring the temperature and pressure of the gas.

56. The method of claim 52 wherein the step of acquiring further comprises the step of analyzing the transmitted light at a sensor comprising a charge coupled device (CCD) array.

57. The method of claim 52 further comprising providing the spectrograph and the sensor in an explosion resistant housing.

58. The method of claim 52 further comprising providing a broadband light source.

59. The method of claim 52 further comprising measuring the spectrum at a pipeline pressure of 192 psi or higher.

60. The system of claim 38 wherein the pressure of the natural gas is 192 psi or higher.

* * * * *